United States Patent [19]

Crisp et al.

[11] 4,143,018

[45] Mar. 6, 1979

[54] CEMENTS

[75] Inventors: Stephen Crisp, Hounslow; Alan D. Wilson, Liphook, both of England

[73] Assignee: National Research Development Corporation, England

[21] Appl. No.: 622,801

[22] Filed: Oct. 16, 1975

[30] Foreign Application Priority Data

Oct. 24, 1974 [GB] United Kingdom ............... 46022/74

[51] Int. Cl.² ............................................. C08K 3/40
[52] U.S. Cl. .................................. 260/29.6 M; 32/15;
106/52; 260/29.6 RW; 260/29.6 H; 260/42.43;
260/998.11
[58] Field of Search ................. 260/29.6 RW, 998.11,
260/42.43, 296 H, 296 M

[56] References Cited

U.S. PATENT DOCUMENTS

| 3,751,391 | 8/1973 | Smith | 260/998.11 |
|---|---|---|---|
| 3,826,778 | 7/1974 | Dietz | 260/998.11 |
| 3,882,080 | 5/1975 | Schmitt et al. | 260/998.11 |
| 3,962,267 | 6/1976 | Suzuki et al. | 260/998.11 |

FOREIGN PATENT DOCUMENTS 1,316,129  5/1973  United Kingdom.

*Primary Examiner*—James H. Derrington
*Attorney, Agent, or Firm*—Jacobs & Jacobs

[57] ABSTRACT

A poly(carboxylate) cement pack comprises as one component a water soluble poly(carboxylic acid) or a precursor thereof, and as another component an aluminosilicate glass, the ratio of acidic to basic oxides in the glass being selected such that the glass will react with a poly(carboxylic acid) in the presence of water to form a poly(carboxylate) cement.

22 Claims, No Drawings

CEMENTS

This invention relates to poly(carboxylate) cements and is an improvement in or modification of the invention described in British Pat. No. 1,316,129.

Poly(carboxylate) cements are formed by the reaction of a poly(carboxylic acid) and an ion-leachable inorganic compound. Such cements are described and claimed for example in British Pat. No. 1,316,129 in which the ion-leachable inorganic compound is a fluoroaluminosilicate glass powder wherein the ratio by weight of silica to alumina is from 1.5 to 2.0 and the ratio by weight of fluorine to alumina is from 0.6 to 2.5 or wherein the ratio by weight of silica to alumina is from 0.5 to 1.5 and the ratio by weight of fluorine to alumina is from 0.25 to 2.0. The poly(carboxylate) cements were originally developed primarily for dental and surgical applications, in which comparatively small quantities of material are used. However, the relatively high fluorine content of these glasses previously required makes them rather difficult and expensive to manufacture on a large scale, and thus it has not up to now proved possible to develop poly(carboxylate) cements for large volume applications.

It has now been found that the fluorine content of the ion-leachable aluminosilicate glass may be reduced to a low value, and in some cases even eliminated, by appropriate control of the basicity of the glass.

According to the present invention there is provided a poly(carboxylate) cement pack comprising as one component a water soluble poly(carboxylic acid) or a precursor thereof, and as another component an aluminosilicate glass, the ratio of acidic to basic oxides in the glass being selected such that the glass will react with a poly(carboxylic acid) in the presence of water to form a poly(carboxylate) cement.

The invention also provides a process for the preparation of a poly(carboxylate) cement which comprises mixing a water soluble poly(carboxylic acid) or a precursor thereof with an aluminosilicate glass in the presence of water, the ratio of acidic to basic oxides in the glass having been selected such that the glass will react with the poly(carboxylic acid) to form a poly(carboxylate) cement.

In this specification the glass compositions are described in the conventional manner as containing alumina, silica, calcium oxide, sodium oxide and other oxides though it is to be understood that these oxides are chemically combined in the matrix of the aluminosilicate glass, and are not present as free oxides. The proportions of oxides quoted for the glass compositions refer to the amounts of these oxides (added in some cases as the corresponding carbonates) added to the glass frit.

The weight ratio of the acidic oxides to basic oxides in the aluminosilicate glass is usually chosen such that the poly(carboxylate) cement stiffens within a relatively short period, termed the working time, which is usually less than ten minutes. It has been found that the rate of reaction increased with increasing basicity of the glass and thus the ratio of the oxides can be chosen in order to allow adequate working time to form the cement into a desired shape before it is has set. For many applications it is preferred to attain a working time of about 5 minutes, or less, and then to have the shortest possible setting time in which the set cement hardens and attains an appreciable compressive strength. Preferably the ratio by weight of acidic to basic oxides in the glass is from 0.1 to 3.0 and most preferably from 0.2 to 2.5.

The principal acidic oxide in the aluminosilicate glass is silica, although the glass may also contain minor amounts of phosphorus pentoxide, and boric oxide. The principal basic oxide in the glass is alumina, which, although it has amphoteric properties, can be considered for the purposes of the present specification solely as a basic oxide. Particularly preferred aluminosilicate glasses fall within the composition range of 10 to 65% w/w silica, and 15 to 50% w/w alumina.

The aluminosilicate glass desirably contains at least one other basic oxide, preferably calcium oxide, which may be present in the glass composition in an amount of from 0 to 50% w/w. The calcium oxide may be partly or wholly replaced by sodium oxide or another basic oxide or mixture of basic oxides, although in some applications the presence of sodium oxide may be undesirable as this oxide tends to increase the solubility of the resultant cement.

Preferred glasses for use in the present invention containing alumina, silica and calcium oxide are the gehlenite and anorthite glasses, and in general glasses falling within the composition range 10 to 65% w/w silica, 15 to 50% w/w alumina and 0 to 50% w/w calcium oxide. Certain of the glasses within this general range, more particularly those having a weight ratio of calcium oxide to silica greater than 0.92 or having a weight ratio of calcium oxide to alumina less than 0.74 are new materials and are accordingly included within the invention.

The aluminosilicate glasses of the present invention may be prepared by fusing mixtures of the components in the appropriate proportions at temperatures above 900° C. and preferably in the range of 1050° C. to 1550° C. The mixture is preferably fused for from 1 to 4 hours. Silica and alumina may be included in the mixture as oxides, but it is convenient to add calcium oxide and sodium oxide as calcium carbonate and sodium carbonate respectively, and references to the presence of these oxides in the glass fusion mixture includes the possibility that they may be added as carbonates or as other compounds which decompose similarly under glass fusion conditions to give the oxides.

The addition of carbonates to the fusion mixture lowers the fusion temperature and thus these can be considered as fluxing agents. If desired, however, the mixture may contain an additional fluxing agent, and this has been found to be important with glass compositions containing less than 10% w/w of calcium oxide. In this connection fluorides such as fluorite and cryolite have been found to be especially useful as fluxing agents, although as previously mentioned it is desirable not to use large amounts of fluorides in the fusion mixture. Accordingly the amount of fluorine in the composition is preferably less than 14% by weight, most preferably less than 8% by weight, based on the total weight of the composition. It has been found that very good results may be obtained using fluorite ($CaF_2$) as a fluxing agent in an amount such that the fluorite is less than 15%, or greater than 90%, on a molar basis, of the total amount of fluorite and calcium oxide present in the glass composition. Other fluxing agents, for example calcium phosphate and aluminium phosphate may also be used, though these are less preferred. The total amount of fluxing agents present in the mixture, including carbonates, may be up to 50% by weight, based on the total weight of the mixture.

After fusion the glass may be poured off and cooled rapdily, for example, in air or water or some combination of both. To a first approximation the proportions of the different elements in the glass may be taken as the proportions of the same elements present in the mixture. Some fluorine may, however, be lost from a fluoride fluxing agent during the reaction.

The glasses used in the present invention may be readily obtained in fine powder form. The degree of fineness of the powder should preferably be such that it produces a smooth cement paste which sets within an acceptable period when mixed with the poly(carboxylic acid) in the presence of water. Preferably the degree of fineness of the powder is such that it will pass through a 150 mesh B.S. sieve and most preferably such that it will pass through a 350 mesh B.S. sieve. Mixtures of different glasses may be used if desired.

The preferred poly(carboxylic acid)s are those prepared by the homopolymerisation and copolymerisation of unsaturated aliphatic carboxylic acids for example acrylic acid, itaconic acid, mesaconic acid, citraconic acid and aconitic acid, and copolymerisation of these acids with other unsaturated aliphatic monomers, for example acrylamide and acrylonitrile. Particularly preferred are the homopolymers of acrylic acid, and co-polymers thereof, in particular copolymers of acrylic acid and itaconic acid as described and claimed in British patent application No. 39383/73. It is also possible to use a precursor of a poly(carboxylic acid) which will be transformed into the poly(carboxylic acid) on contact with water, for example a poly(carboxylic acid anhydride) or other suitable polymer. The poly(carboxylic acid anhydride) may be a homopolymer of an unsaturated carboxylic acid anhydride, or a copolymer with a vinyl monomer, and particularly a vinyl hydrocarbon monomer. Good results may be obtained using homopolymers of maleic anhydride and copolymers thereof with ethylene, propene, butene and styrene.

The poly(carboxylic acid) or precursor thereof is preferably linear although branched polymers may also be used, and preferably has an average molecular weight of from 1000 to 250,000 and most preferably from 5000 to 100,000. In this specification, the average molecular weight is that measured by an absolute method such as light scattering or ultracentrifuge sedimentation.

Cement packs in accordance with this invention preferably comprise the poly(carboxylic acid) in the form of an aqueous solution containing from 20 to 65% by weight of the poly(carboxylic acid). The cement pack may be a two-part pack in which the weight ratio of aluminosilicate glass to liquid in the two parts is from 0.5:1 to 5:1 and preferably from 1.5:1 to 4.5:1, so that when the entire contents of the pack are mixed together a rapidly hardening cement is obtained. In another embodiment the pack may contain the glass and the liquid in separate capsules, the total amount of glass in the pack and the total amount of liquid in the pack being in the appropriate ratio. In a further embodiment, both components may be encapsulated in the same capsule in the desired ratio, provided that steps are taken to prevent premature reaction. In a still further embodiment the pack may comprise an intimate mixture of the aluminosilicate glass and the poly(carboxylic acid) in powder form, the total amount of the components in the mixture being in the appropriate ratio. Water may be included in this embodiment provided that the pack is provided with means to prevent premature reaction.

In the above mentioned embodiments the aluminosilicate glass is preferably from 15 to 85% by weight, the poly(carboxylic acid) is preferably from 3 to 50% by weight, and the water is preferably from 5 to 70% by weight, based on the total weight of the components.

The poly(carboxylate) cements of this invention may be made up in the conventional manner. Thus the materials in the one or two-part pack are brought together and mixed forming a plastic mass which can be cast, moulded, or otherwise formed in the required shape during the brief period in which the mixture retains its plastic properties. The components can be mixed quite rapidly to give a uniform mass which commences to harden in a few minutes and is usually set within 10 minutes of mixing. The rate of hardening and strength of the final product are partly determined by the glass/liquid ratio which is preferably as high as possible compatible with adequate working time. The optimum ratio for a particular aluminosilicate glass and poly(carboxylic acid) may be determined readily with preliminary experiments. Too little or too much glass normally results in a mixture that is more difficult to form into a desired shape. Particularly good results have been obtained using the components in the ratio of 2 to 10 parts by weight of aluminosilicate glass for each part by weight of the poly(carboxylic acid) or precursor thereof. For a given system, an improvement in the working time and a reduction in the setting time together with an increase in compressive strength may frequently be obtained by the addition of a water soluble chelating agent to the mixture as described in British patent application No. 17880/72, which is incorporated herein by reference thereto.

The poly(carboxylate) cements of the present invention may find application in dentistry, and also in orthopaedic surgery where they may be used to assist in the resetting of fractured bone material and in the production of water hardenable surgical dressings. They are particularly useful for cementing in moist environments and may find application as grouting cements. In addition they may be useful as binders, for example in foundry sand casting techniques.

The invention is illustrated by the following Examples:

EXAMPLE 1

A series of glasses are prepared by fusing mixtures of silica, alumina, calcium and sodium carbonates as set out in Table 1 below in a platinum crucible. After fusion the glass is poured off and cooled rapidly. The glass compositions and fusion conditions are as follows:

TABLE 1

|  | I | II | III |
|---|---|---|---|
| $SiO_2$ | 118 | 143 | 118 |
| $Al_2O_3$ | 100 | 100 | 100 |
| CaO* | 110 | 32 | 55 |
| $Na_2O$* | — | 20 | — |
| Fusion temperature (° C) | 1400 | 1500 | 1550 |
| Time (hours) | 2¼ | 3¾ | 1 |

*added as carbonates to the fusion mixture.

The resultant glasses are dried and crushed until they pass through a 350 mesh B.S. sieve.

Cements are prepared by mixing the crushed glasses with a 47.5% w/w aqueous solution of an acrylic acid/itaconic acid copolymer containing 47.4% itaconic acid units prepared as described in British patent application No. 39383/73. The properties of the cements are set out in Table 2:

TABLE 2

|  | I | II | III |
|---|---|---|---|
| Setting time in minutes (using a 1 lb. Gilmore needle at 37° C) | 2.25 | 3.75 | 4.0 |
| Compressive strength developed after 24 hrs. at 37° C (Nmm$^{-2}$) | 74 | 61 | 56 |
| Powder/liquid ratio (g/ml) | 2.5 | 2.75 | 3.0 |

All the set cements prepared are found to be hydrolytically stable.

EXAMPLE 2

The following compounds are mixed by milling and then heated in a sillimanite crucible at 1250° C. until homogeneous (about 3 hrs).

| Silica | 143 gms. |
|---|---|
| Alumina | 100 gms. |
| Cryolite | 76 gms. |
| Fluorite | 56 gms. |
| Aluminium phosphate | 73 gms. |

The glass is prepared as described in Example 1 and crushed until it passes through a 350 mesh B.S. sieve. The glass is found to have a fluorine content of about 13.5% by weight (determined by the method of A. C. D. Newman in 'Analyst', 1968 vol. 93 page 827).

A cement is prepared by mixing the crushed glass with a 47.5% w/w aqueous solution of an acrylic acid-/itaconic acid copolymer containing 47.4% itaconic acid units, prepared as described in Example 2 of British patent application No. 39383/73 at a powder/liquid ratio of 2.5. The properties of the cement are as follows:

| Setting time in minutes (using a 1 lb. Gilmore needle at 37° C) | 3.5 |
|---|---|
| Compressive strength developed after 24 hrs. at 37° C (Nmm$^{-2}$) | 157 |

EXAMPLE 3

A series of glasses are prepared by fusing mixtures of compounds in amounts and at fusion conditions as listed in Table 3 (separate sheet).

TABLE 3

|  | A | B | C | D | E | F | G | H | I |
|---|---|---|---|---|---|---|---|---|---|
| SiO$_2$ | 180 gms | 60 gms | 120 gms | 240 gms | 87 gms | 286 gms | 120 gms | 240 gms | 120 gms |
| Al$_2$O$_3$ | 102 gms | 102 gms | 102 gms | 102 gms | 102 gms | 200 gms | 102 gms | 102 gms | 102 gms |
| CaO* | 56 gms | 112 gms | 93 gms | 168 gms | 78 gms | 64 gms | 168 gms | 112 gms | 101 gms |
| Na$_2$O* |  |  |  |  |  | 39 gms |  |  |  |
| CaF$_2$ |  |  | 26 gms |  |  |  |  |  | 156 gms |
| Fusion temperature (° C) | 1500–1550 | 1400–1550 | 1450 | 1450 | 1430 | 1400–1500 | 1525 | 1430–1500 | 1450 |
| Time | 4 hrs | 85 min | 90 min | 90 min | 90 min | 2¼ hrs | 85 min | 2 hrs | 90 min |

*added as carbonates to the fusion mixture

The resultant glasses are dried and crushed until they pass through a 350 mesh B.S. sieve.

Cements are prepared by mixing the crushed glasses with a 47.5% w/w aqueous solution of an acrylic acid-/itaconic acid copolymer containing 5% by weight of tartaric acid, the copolymer having 47.4% itaconic acid units, prepared as described in Example 2 of British patent application No. 39383/73.

The properties of the cements are set out in Table 4 (separate sheet).

TABLE 4

|  | A | B | C | C | D | E | E | F | F | G | G | H | I |
|---|---|---|---|---|---|---|---|---|---|---|---|---|---|
| Powder/liquid ratio (g/ml) | 3 | 7 | 2 | 2½ | 1 | 2 | 2½ | 2½ | 2¾ | 2 | 2½ | 3 | 2½ |
| Working time (mins)* | 5¼ | 2¼ | ¾ | ½ | 1 | 2 | 1½ | 1½ | 1¼ | ½ | 1¼ | ¾ | ¾ |
| Setting time (mins) (using a 1 lb Gilmore needle at 37° C) | 8¼ | 3½ | 2½ | 2¼ | 5 | 3¼ | 3¼ | 3¾ | 3¾ | 2¾ | 2¼ | 4 | 2¼ |
| Compressive strength (N/mm$^2$) | 29 | 104 | 120 |  | 30 | 87 | 96 | 56 |  | 61 | 95 |  35 | 125 |
| Diametral strength (N/mm$^2$) | 4.5 | 11.0 | 11.9 |  |  |  |  |  |  |  | 11.8 |  | 12.3 |
| Solubility (%) |  | 0.11 | 0.14 |  | 0.55 | 0.2 | 0.16 | 1.34 |  |  | 0.21 |  | 1.42 |

*Measured using a 28 gram Gilmore needle of 1.05 mm diameter, taking the time at which the needle no longer makes an impression of 0.5 mm.

We make no claim to anything described or claimed in British Patent Specification No. 1,316,129.

We claim:

1. A water hardenable cement composition which comprises a poly(carboxylic acid) or anhydride thereof which forms the poly(carboxylic acid) in the presence of water, an aluminosilicate glass comprising from 0 up to 8 percent by weight of fluorine, the ratio of acidic to basic oxides in the glass being from 0.1 to 3.0 that the glass will react with said poly(carboxylic acid) in the presence of water to form a poly(carboxylic) cement, and a water soluble chelating agent.

2. A composition, according to claim 1, in which the poly(carboxylic acid) is a polymer of acrylic acid.

3. A composition, according to claim 1, in which the poly(carboxylic acid) is a copolymer of acrylic acid and itaconic acid.

4. A composition, according to claim 1, in which the aluminosilicate glass has a composition comprising from 10 to 65% by weight of silica, from 15 to 50% by weight of alumina and from 0 to 50% by weight of calcium oxide, based on the total weight of the composition.

5. A composition, according to claim 4, in which the aluminosilicate glass has a composition in which the weight ratio of calcium oxide to silica is greater than 0.92 or in which the weight ratio of calcium oxide to alumina is less than 0.72.

6. A composition, according to claim 1, in which the glass has a composition comprising fluorine.

7. A composition, according to claim 1, in which the aluminosilicate glass is in the form of a powder having a degree of fineness such that it will pass through a 150 mesh B.S. sieve.

8. A composition, according to claim 1, in which the poly(carboxylic acid) is in the form of an aqueous solution containing from 20 to 65% by weight of the poly(carboxylic acid).

9. A composition, according to claim 10, in which the weight ratio of aluminosilicate glass to said equeous solution is from 0.5:1 to 5:1.

10. A composition, according to claim 8, in which the aluminosilicate glass is present in an amount of from 15 to 85% by weight, the poly(carboxylic acid) is present in an amount of from 3 to 50% by weight, and water is present in an amount of from 5 to 70% by weight, based on the total weight of the composition.

11. A process for the preparation of a poly(carboxylate) cement which comprises mixing a water soluble poly(carboxylic acid) or anhydride thereof which forms the poly(carboxylic acid) in the presence of water with an aluminosilicate glass comprising from 0 up to 8 per cent by weight of fluorine and a water soluble chelating agent in the presence of water, the ratio of acidic to basic oxides in the glass being from 0.1 to 3.0 such that the glass will react with said poly(carboxylic acid) to form a poly(carboxylate) cement.

12. A process according to claim 11, in which the poly(carboxylic acid) is a polymer of acrylic acid.

13. A process according to claim 11, in which the poly(carboxylic acid) is a copolymer of acrylic acid and itaconic acid.

14. A process according to claim 11, in which the glass has a composition comprising from 10 to 65% by weight of silica, from 15 to 50% by weight of alumina and from 0 to 50% by weight of calcium oxide, based on the total weight of the composition.

15. A process according to claim 11, in which the aluminosilicate glass has a composition in which the weight ratio of calcium oxide to silica is greater than 0.92 or in which the weight ratio of calcium oxide to alumina is less than 0.72.

16. A process according to claim 11, in which the glass has a composition comprising fluorine.

17. A process according to claim 11, in which the aluminosilicate glass is in powder form, the powder having a degree of fineness such that it will pass through a 150 mesh B.S. sieve.

18. A process according to claim 11, in which the poly(carboxylic acid) is in the form of an aqueous solution, comprising from 20 to 65% by weight of the poly(carboxylic acid).

19. A process according to claim 18, in which the aluminosilicate glass and the poly(carboxylic acid) solution are mixed in a weight ratio of from 0.5:1 to 5:1.

20. A process according to claim 11, in which the aluminosilicate glass is present in an amount of from 15 to 85% by weight, the poly(carboxylic acid) is present in an amount of from 3 to 50% by weight, and water is present in an amount of from 5 to 70% by weight, based on the total weight of the composition.

21. A process accordingly to claim 13 in which the aluminosilicate glass is a gehlenite or anorthite glass.

22. A poly(carboxylate) cement produced by the process accroding to claim 11.